| United States Patent [19] | [11] Patent Number: 4,486,275 |
|---|---|
| Emmenegger | [45] Date of Patent: Dec. 4, 1984 |

[54] SOLUTION FOR ELECTROPLATING A GOLD-COPPER-CADMIUM ALLOY

[76] Inventor: Heinz Emmenegger, Rue du Locle 3a, La-Chaux-de-Fonds, Switzerland

[21] Appl. No.: 577,529

[22] Filed: Feb. 6, 1984

[30] Foreign Application Priority Data

Feb. 7, 1983 [CH] Switzerland ............................ 682/83
Jun. 10, 1983 [CH] Switzerland .......................... 3180/83

[51] Int. Cl.$^3$ ............................................... C25D 3/62
[52] U.S. Cl. ..................................................... 204/44
[58] Field of Search ................................. 204/44, 123

[56] References Cited

U.S. PATENT DOCUMENTS

| | | | |
|---|---|---|---|
| 3,056,733 | 10/1962 | Heilmann | 204/44 |
| 3,586,611 | 6/1971 | Heilmann | 204/44 |
| 4,179,344 | 12/1979 | Thomson | 204/44 |
| 4,309,256 | 1/1982 | Aliprandini | 204/44 |

*Primary Examiner*—G. L. Kaplan
*Attorney, Agent, or Firm*—Lyon & Lyon

[57] ABSTRACT

A bath and method for electrodepositing gold-copper-cadmium alloys. The electroplating solution contains cadmium ions complexed by a soluble hydroxyalkyl diacetate complexing agent and, in addition, a brightener in the form of a phosphoric ester of a chain of ethylene oxides bonded to an alkyl group, and/or a surfactant in the form of one or a mixture of more than one amidopropyldimethylaminoxides of fatty acids.

12 Claims, No Drawings

SOLUTION FOR ELECTROPLATING A GOLD-COPPER-CADMIUM ALLOY

This invention relates to the art of electroplating, and more particularly to a solution for the electrolytic deposition of a gold-copper-cadmium alloy, a method of using this solution, and an article obtained by this method.

The electrolytic deposition of a gold-copper-cadmium alloy has taken on great importance because it yields a bright, workable coating, although relatively thick, of gold alloy, the color of which may vary from pale yellow to pink, while still retaining a gold content of from 12 to 20 karats. Gold-copper alloys including a white metal to give them a paler, more yellowish color have been used for many years. At present, cadmium is accepted to have the best electrochemical qualities required for being deposited together with gold and copper.

Numerous patents describe methods relating to the deposition of such gold-copper-cadmium alloys, particularly U.S. Pat. No. 4,309,256 and Swiss Pat. Nos. 542,934, 556,916, and 621,367, which are representative of the state of the art forming the point of departure for the present invention. All these methods use cyanided solutions containing a complex gold cyanide, a complex copper cyanide, potassium cyanide, a complex organic cadmium salt stable enough to exist in a cyanided solution, and an organic brightening agent. In these plating solutions, two chemical agents control the mechanism of deposition, viz., the cadmium complexing agent and the brightener; for although the gold-copper alloy is normally deposited from the complex cyanides of these metals, the cadmium must necessarily be obtained from an organic complex which makes it possible to stabilize the cadmium content of the alloy deposited. If a complex cyanide were also used, without chelating agent, for the cadmium, either brittle, white deposits would be obtained, or else the cadmium content of the plating solution would have to be maintained at very low levels, which would present problems as regards the regeneration and useful life of the solution. On the other hand, it is economically necessary to obtain a bright deposit even for thicknesses of 30 or 40 microns. It is therefore important to add brightening agents to the electrolytic solution, for otherwise the deposit is dull and requires polishing, always an expensive operation.

The complexing agents used to regulate the amount of cadmium in the electrolytically deposited gold-copper-cadmium alloy are most often soluble organic products, the molecule of which contains one or more atoms of nitrogen and carboxylic acid groups which ensure the solubility. Thus, the aforementioned Swiss Pat. Nos. 542,934 and 556,916 relate to the use of ethylene diamine tetraacetic acid (EDTA) and nitrilotriacetic acid (NTA), U.S. Pat. No. 4,309,256 to the use of NTA alone, and Swiss Pat. No. 621,367 to the use of compounds containing nitrogen and carboxylated propyl groups.

Experience has shown that NTA and EDTA strongly complex the cadmium. Hence the concentrations of cadmium and complexing agent must be kept within rather strict limits, which does not allow a very flexible control of the solution. If the concentration of complexing agent is too low, the deposit becomes too pale, and if it is too high, the deposit becomes pink because the cadmium is no longer deposited. The gold-copper-cadmium alloy is then easily attacked by nitric acid, which is not the case when the alloy is correct. The aforementioned Swiss Pat. No. 621,367 mentions these shortcomings and proposed remedying them by using complexing agents having a molecule comprising several carboxylated propyl groups. Since the stability constant of the cadmium complexes of these products is less than that of NTA AND EDTA, such compounds may be present in the solution in a relatively broad range of concentrations. However, when the concentration is too low, secondary effects cause brittle deposits with poor homogeneity, whereas an excess leads to pitted deposits and uneven thicknesses.

It is an object of this invention to provide an improved electroplating solution and method of depositing a gold-copper-cadmium alloy whereby the solution can be more easily controlled than is possible in the case of the prior art.

To this end, the solution according to the present invention comprises a complex gold cyanide, a complex copper cyanide, cadmium ions, free potassium cyanide, a wetting agent as a brightener and a complexing agent of the general formula

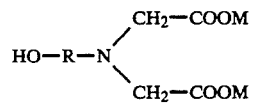

wherein R signifies an alkylene group having 1–4 carbon atoms, and M signifies sodium, potassium or ammonium ions.

The proposed electrolytic solution contains complexing agents having a stability constant better adapted to the simultaneous deposition of cadmium, gold, and copper than that of the prior art complexing agents. The present agents are of the hydroxyalkylaminodicarboxylic type of the general formula

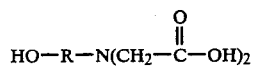

wherein R signifies an alkylene group having 1–4 carbon atoms. The stability constant of these compounds is on the order of 9 when R is a methyl group, 7.5 when R is an ethyl group, 6.2 for a propyl group, and about 5 for a butyl group. The presence of the hydroxy group seems particularly important for conferring on these molecules a stability constant favorable to the co-deposition of the cadmium with the gold and the copper in a cyanided medium. The carboxylic acid group must not comprise more than two carbon atoms. With three carbon atoms, the stability constant is too low to permit good co-deposition of the cadmium in the presence of potassium cyanide. Whereas the complexing agent margin for obtaining a correct deposit is only 4–6 g/liter with NTA and 0.8–1.0 g/liter with EDTA, the complexing agents present in the solution proposed by the present invention and, in particular, sodium, potassium, or ammonium hydroxyalkylimino diacetate, may be added with a much larger margin for maneuver, in quantities up to ten times as great, without changing the qualities of the gold-copper-cadmium alloy deposit as regards both its color and its resistance to corrosion.

Besides the cadmium ion complexing agent, solutions for depositing a gold-copper-cadmium alloy generally contain a product intended to produce a bright deposit, even for very thick coatings. To achieve this, organic molecules are used which act at the level of the layer of electrolyte closest to the surface to be coated and which influence the diffusion of the metal ions through that surface by varying the surface tension of the liquid. Hence these products act upon the crystallization of the alloy deposited. The patents previously mentioned disclose the use of the phosphoric ester of the condensation product of nonyl phenol and a chain of ethylene oxides, substances having a molecule comprising both an aliphatic chain and a benzene nucleus, or the use of a polyoxyalkylene derivative. It has been found, however, that these products cause irregularities in the form of pits or craters in the alloy deposited as soon as their concentration exceeds a certain maximum, so that they can be used only within a narrow margin of concentrations.

For this reason, the solution proposed by the present invention also preferably includes, as brighteners in the solution for electrolytic deposit of a gold-copper-cadmium alloy, products having a molecule comprising only aliphatic chains bonded to a phosphoric ester of a chain of ethylene oxides. In particular, products corresponding to the following general formulae have been used successfully:

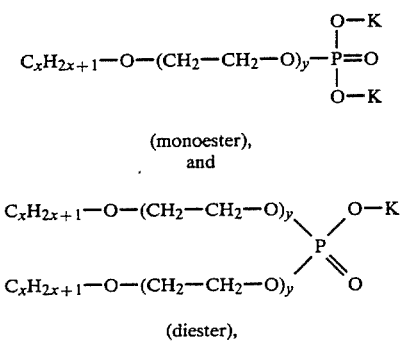

(monoester),
and (diester), wherein x signifies a number from 8–18 and y signifies a number from 6–15. The molecular weight of these various compounds is from 600 to 800 for the monoesters and from 800 to 2000 for the diesters. The alkyl chains may be straight or branched (iso).

Such products having an aliphatic chain are much better tolerated by the constituents of the solution than those where the molecule contains a benzene nucleus, and as a result it is possible to use concentrations from five to ten times higher, in the form of sodium, potassium, or ammonium salts, which are easily soluble.

According to the present invention, there is used alternatively a surfactant which would act at the same time as a brightening agent; in particular, the amidopropyldimethylaminoxide-type derivatives of fatty acids corresponding to the following general formula have been used successfully:

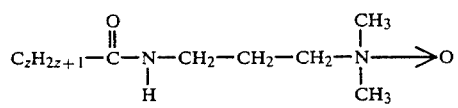

wherein z signifies a number from 11–17. Such amidopropyldimethylaminoxide derivatives of fatty acids are much better tolerated by the constituents of the solution than the polyoxyalkylene compounds and may therefore be used in concentrations from 10 to 20 times higher.

The electrolytic solutions for depositing a gold-copper-cadmium alloy according to the present invention are preferably used at a pH of 9–11, with a current density of 0.6 to 1.5 amps/sq. dm., and at a temperature of 50°–75° C. Agitation or stirring of the parts subjected to this process is necessary to ensure uniform distribution of the current and, consequently, uniform thickness of the deposit. The concentrations of the diverse constituents of these solutions must each be situated within a range which has been determined experimentally. Thus, the gold, in the form of a complex cyanide, must be present at from 1–20 g/liter, preferably 3–5 g/liter; the copper, likewise in the form of a complex cyanide, from 6–70 g/liter, preferably 40–65 g/liter; and the cadmium, in the form of cyanide, an inorganic salt such as sulfate, for example, or a complex organic salt, from 0.3 to 5 g/liter, preferably 0.5 to 2.5 gram/liter. The concentration of free potassium cyanide may vary from 3–40 g/liter. The concentration of organic cadmium-complexing agent, especially of sodium, potassium, or ammonium hydroxyalkylimino diacetate, may vary from 5 to 100 g/liter, preferably 7.5–20 g/liter. Finally, the brightener in the form of a phosphoric ester of a chain of ethylene oxides having 6–15 carbon atoms bonded to an alkyl group having 8–18 carbon atoms, may be present within the limits of 5–20 cc/liter, preferably 5–7.5 cc/liter, and the surfactant, in the form of an amidopropyldimethylaminoxide-type derivative of fatty acids, may be present within the limits of 0.1 to 50 ml/liter. To increase the conductivity of the solution between the electrodes, it is necessary to add alkaline salts such as carbonates, borates, or phosphates, in amounts from 10–40 g/liter, which also act as pH regulators.

The following examples illustrate various preferred possibilities of depositing gold-copper-cadmium alloys of different compositions.

EXAMPLE 1

| Composition of solution: | |
|---|---|
| Gold, in form of complex cyanide | 4 g/l |
| Copper, in form of complex cyanide | 65 g/l |
| Cadmium, in form of cyanide | 1 g/l |
| Free potassium cyanide | 27 g/l |
| Potassium hydroxyethylimino diacetate | 25 g/l |
| Wetting agent (phosphoric ester of a chain of 10 molecules of ethylene oxide bonded to an alkyl chain having 8 carbon atoms) | 5 ml/l |
| Dipotassium phosphate | 20 g/l |
| pH | 10.5 |

A 5×2 cm steel plate was plated in this solution at a current density of 0.75 amps/sq. dm. and a temperature of 60° C. It was coated with a bright, uniform deposit, pale pink of color 4 N, having the following composition:

| gold | 55.4% | (thus 13.3 kt). |
|---|---|---|
| copper | 36.1% | |
| cadmium | 6.9% | |

Using EDTA or NTA complexing agents, it would not be possible to obtain a pale pink 4 N deposit under these conditions. Only a red deposit with a little cadmium would be obtained.

EXAMPLE 2

| Composition of solution: | |
|---|---|
| Gold, in form of complex cyanide | 4 g/l |
| Copper, in form of complex cyanide | 65 g/l |
| Cadmium, in form of cyanide | 1.25 g/l |
| Potassium hydroxyethylimino diacetate | 25 g/l |
| Free potassium cyanide | 27 g/l |
| Wetting agent (phosphoric ester of a chain of 10 molecules of ethylene oxide bonded to an alkyl chain having 10 carbon atoms) | 5 ml/l |
| Dipotassium phosphate | 20 g/l |
| pH | 10.5 |

A 5×2 cm steel plate was likewise plated in this solution at a current density of 0.75 amps/sq. dm. and a temperature of 60° C. It was coated with a pinkish deposit of color 3–4 N, having the following composition:

| gold | 62.1% | (thus 14.9 kt). |
|---|---|---|
| copper | 28% | |
| cadmium | 9.5% | |

EXAMPLE 3

| Composition of solution: | |
|---|---|
| Gold, in form of complex cyanide | 4 g/l |
| Copper, in form of complex cyanide | 65 g/l |
| Cadmium, in form of cyanide | 1.5 g/l |
| Sodium hydroxyethylimino diacetate | 25 g/l |
| Free potassium cyanide | 27 g/l |
| Wetting agent (phosphoric ester of a chain of 10 molecules of ethylene oxide bonded to an alkyl chain having 12 carbon atoms) | 5 ml/l |
| pH (to be corrected with a 20% solution of phosphoric acid) | 10 |

A 5×2 cm steel plate was plated in this solution at a current density of 0.75 amps/sq. dm. and a temperature of 60° C. for 30 minutes. It was coated with a uniform, bright yellow deposit of color 2–3 N, having the following composition:

| gold | 66% | (thus 16 kt). |
|---|---|---|
| copper | 23.5% | |
| cadmium | 10.5% | |

EXAMPLE 4

| Composition of solution: | |
|---|---|
| Gold, in form of complex cyanide | 4 g/l |
| Copper, in form of complex cyanide | 60 g/l |
| Cadmium, in form of cyanide | 1 g/l |
| Sodium hydroxymethylimino diacetate | 15 g/l |
| Wetting agent (phosphoric ester of a chain of 10 molecules of ethylene oxide bonded to an alkyl chain having 8 to 10 carbon atoms) | 1 ml/l |
| Free potassium cyanide | 30 g/l |
| Dipotassium phosphate | 20 g/l |
| pH | 10 |

A 5×2 cm plate was plated in this solution at a current density of 0.6 amps/sq. dm and a temperature of 55° C. It was coated with a bright, very even deposit of color yellow 2N 18, having the following composition:

| gold | 75% | (thus 18 kt). |
|---|---|---|
| copper | 17% | |
| cadmium | 8% | |

EXAMPLE 5

| Composition of solution: | |
|---|---|
| Gold, in form of complex cyanide | 4 g/l |
| Copper, in form of complex cyanide | 70 g/l |
| Cadmium, in form of cyanide | 1 g/l |
| Potassium hydroxyethylimino diacetate | 10 g/l |
| Free potassium cyanide | 25 g/l |
| Wetting agent (phosphoric ester of a chain of 10 molecules of ethylene oxide bonded to an alkyl chain having 8 carbon atoms) | 5 ml/l |
| Dipotassium phosphate | 20 g/l |

A 5×2 cm steel plate was plated in this solution at a current density of 1 amps/sq. dm. and a temperature of 58° C. It was coated with a bright, homogeneous, yellow deposit of gold-copper-cadmium alloy at a rate of 10 microns per 20 minutes. It had the following composition:

| gold | 67% | (thus 16 kt). |
|---|---|---|
| copper | 23% | |
| cadmium | 10% | |

The film of alloy is particularly ductile. In this connection, it should be noted that according to the prior art, it would be necessary to use a concentration of 2.5 g/liter of cadmium ions and a current density of 1.8–3.0 amps/sq. dm. in order to obtain a yellow deposit of 16-kt gold-copper-cadmium alloy. Under these conditions, the deposit is yellow but brittle, apparently owing to the co-deposition of hydrogen at these relatively high current densities. Example 5 shows that with the method now proposed, it is possible to obtain a 16-kt yellow deposit which is really ductile with a current density of only 1 amp/sq. dm. and a cadmium-ion content in the solution of only 1 g/liter.

EXAMPLE 6

| Composition of solution: | |
|---|---|
| Gold, in form of complex cyanide | 4 g/l |
| Copper, in form of complex cyanide | 50 g/l |
| Cadmium, in form of complex cyanide | 0.8 g/l |
| Potassium hydroxypropylimino diacetate | 25 g/l |
| Free potassium cyanide | 25 g/l |
| Wetting agent (phosphoric ester of a chain of 10 molecules of ethylene oxide bonded to an alkyl chain having 10 carbon atoms) | 5 ml/l |
| pH (to be corrected with a 20% solution of phosphoric acid) | 10 |

The test was carried out in a Hull cell at 0.5 amps and at 60° C. for 10 minutes. The plate was coated with a deposit going from yellow for the low current densities to pink for the high current densities, uniformly bright.

EXAMPLE 7

In this example, the same solution was used as in Example 6, but with a potassium hydroxypropylimino diacetate concentration of 100 g/liter, thus quadrupling the concentration. The test was carried out in a Hull cell at 0.5 amps and at 60° C. for 10 minutes. The plate cas coated with a deposit of colors similar to that obtained in Example 6.

EXAMPLE 8

| Composition of solution: | |
|---|---|
| Gold, in form of complex cyanide | 4 g/l |
| Copper, in form of complex cyanide | 65 g/l |
| Cadmium, in form of cyanide | 1 g/l |
| Free potassium cyanide | 27 g/l |
| Potassium hydroxyethylimino diacetate | 25 g/l |
| Wetting agent (amidopropyldimethylaminoxide of saturated fatty acids, between 11 and 17 carbon atoms) | 5 g/l |
| Potassium carbonate | 20 g/l |
| pH | 10.5 |

A 5×2 cm steel plate was plated in this solution at a current density of 0.75 amps/sq. dm and a temperature of 60° C. It was coated with a uniform, bright, pale pink deposit of color 4 N, having the following composition:

| gold | 55.4% | (thus 13,3 kt). |
|---|---|---|
| copper | 36.1% | |
| cadmium | 6.9% | |

Using EDTA or NTA complexing agents, it would not be possible to obtain a pale pink 4 N deposit under these conditions. Only a red deposit with a little cadmium would be obtained.

EXAMPLE 9

| Composition of solution: | |
|---|---|
| Gold, in form of complex cyanide | 4 g/l |
| Copper, in form of complex cyanide | 65 g/l |
| Cadmium, in form of cyanide | 1.25 g/l |
| Potassium hydroxyethylimino diacetate | 25 g/l |
| Free potassium cyanide | 27 g/l |
| Wetting agent (amidopropyldimethylaminoxides of saturated fatty acids, between 11 and 17 carbon atoms) | 5 ml/l |
| Dipotassium phosphate | 20 g/l |
| pH | 10.5 |

A 5×2 cm steel plate was plated in this solution at a current density of 0.75 amps/sq. dm. and a temperature of 60° C. It was coated with a pinkish deposit of color 3-4 N, having the following composition:

| gold | 62.1% | (thus 14.9 kt). |
|---|---|---|
| copper | 28% | |
| cadmium | 9.5% | |

EXAMPLE 10

| Composition of solution: | |
|---|---|
| Gold, in form of complex cyanide | 4 g/l |
| Copper, in form of complex cyanide | 60 g/l |
| Cadmium, in form of cyanide | 0.6 g/l |
| Sodium hydroxyethylimino diacetate | 12 g/l |
| Free potassium cyanide | 25 g/l |
| Wetting agent (amidopropyldimethylaminoxides of saturated fatty acides, between 11 and 17 carbon atoms) | |
| pH | 10.3 |

A 5×2 cm steel plate was plated in this solution at a current density of 0.7 amps/sq. dm. and a temperature of 55° C. It was coated with a yellow deposit of color 2 N 18, assaying 18 karats.

EXAMPLE 11

| Composition of solution: | |
|---|---|
| Gold, in form of complex cyanide | 4 g/l |
| Copper, in form of complex cyanide | 65 g/l |
| Cadmium, in form of cyanide | 1 g/l |
| Sodium hydroxyethylimino diacetate | 12 g/l |
| Free potassium cyanide | 28 g/l |
| Wetting agent (amidopropyldimethylaminoxides of saturated fatty acides, between 11 and 17 carbon atoms) | 40 ml/l |
| pH | 10.3 |

This solution was used to plate brass watch cases, working at a current density of 1 amp/sq. dm. and at 60° C. A bright, 10-micron deposit of a ductile alloy assaying 16 karats of the following composition was obtained:

| Gold | 67% |
|---|---|
| Copper | 23% |
| Cadmium | 10% |

EXAMPLE 12

| Composition of solution: | |
|---|---|
| Gold, in form of complex cyanide | 4 g/l |
| Copper, in form of complex cyanide | 60 g/l |
| Cadmium, in form of cyanide | 1 g/l |
| Sodium hydroxymethylimino diacetate | 15 g/l |
| Free potassium cyanide | 30 g/l |
| Wetting agent (amidopropyldimethylaminoxides of saturated fatty acids, between 11 and 17 carbon atoms) | 2 ml/l |
| Potassium borate | 20 g/l |
| pH | 10.0 |

A 5×2 cm steel was plated in this solution at a current density of 0.6 amps/sq. dm. and a temperature of 55° C. It was coated with a very even, bright deposit of color yellow 2 N 18, having the following composition:

| gold | 75% | (thus 18 kt). |
|---|---|---|
| copper | 17% | |
| cadmium | 8% | |

EXAMPLE 13

| Composition of solution: | |
|---|---|
| Gold, in form of complex cyanide | 4 g/l |
| Copper, in form of complex cyanide | 65 g/l |
| Cadmium, in form of cyanide | 1 g/l |
| Potassium hydroxyethylimino diacetate | 10 g/l |
| Free potassium cyanide | 27 g/l |
| Wetting agent (amidopropyldimethylaminoxides | 20 ml/l |

| Composition of solution: | |
|---|---|
| of saturated fatty acides, between 11 and 17 carbon atoms) | |
| Dipotassium phosphate | 20 g/l |

A 5×2 cm steel plate was plated in this solution at a current density of 1 amps/sq. dm. and a temperature of 58° C. It was coated with a bright, homogenous yellow deposit of gold-copper-cadmium alloy at the rate of 10 microns per 20 minutes. It had the following composition:

| gold | 67% | (thus 16 kt). |
|---|---|---|
| copper | 23% | |
| cadmium | 10% | |

The film of alloy is particularly ductile. In this connection, it should be noted that according to the prior art, it would be necessary to use a concentration of 2.5 g/liter of cadmium ions and a current density of 1.8-3.0 amps/sq. dm. in order to obtain a yellow deposit of 16-kt gold-copper-cadmium alloy. Under these conditions, the deposit is yellow but brittle, apparently owing to the co-deposition of hydrogen at these relatively high current densities. Example 13 shows that with the method now proposed, it is possible to obtain a 16-kt yellow deposit which is really ductile with a current density of only 1 amp/sq. dm. and a cadmium-ion content in the solution of only 1 g/liter.

EXAMPLE 14

| Composition of solution: | |
|---|---|
| Gold, in form of complex cyanide | 4 g/l |
| Copper, in form of complex cyanide | 50 g/l |
| Cadmium, in form of complex cyanide | 0.8 g/l |
| Potassium hydroxypropylimino diacetate | 25 g/l |
| Free potassium cyanide | 25 g/l |
| Wetting agent (amidopropyldimethylaminoxides of saturated fatty acides, between 11 and 17 carbon atoms) | 0.5 ml/l |
| pH (to be corrected with a 20% solution of phosphoric acid). | 10.0 |

The test was carried out in a Hull cell at 0.5 amps and at 60° C. for 10 minutes. The plate was coated with a deposit going from yellow for the low current densities to pink for the high current densities, uniformly bright.

EXAMPLE 15

In this example, the same solution was used as in Example 14 but with a potassium hydroxypropylimino diacetate concentration of 100 g/liter, thus quadrupling the concentration. The test was carried out in a Hull cell at 0.5 amps and at 60° C. for 10 minutes. The plate was coated with a deposit of colors similar to that obtained in Example 14.

It will be seen that when the concentration of the complexing agent used in this invention is greatly increased, the composition of the alloy deposited varies very little; this could not happen with the complexing agents used in the prior art.

The foregoing examples show that the cadmium-complexing agents and the brighteners contained in the solution according to the present invention make it possible to obtain bright, homogeneous, even deposits or gold-copper-cadmium alloys which may range from 12 to 20 karats and more. The concentrations of the cadmium-complexing agents and the brighteners may vary to a wide extend without affecting the quality of the deposit, contrary to what happens in the prior art.

The article treated in the proposed solution, presented by way of example as being a steel plate, may naturally be made of any other conductive material or even of an insulating material covered beforehand with a conductive coating.

The electroplating solution according to this invention and the method utilizing it yield gold-plated articles of all shapes and sizes; and the layer of plating, of 12 to 20-kt gold according to the proportions of the constituents of the solution, may be economically thin or else thick enough to give the article properties similar to those of solid gold articles, particularly jewelry.

What is claimed is:

1. An electroplating solution for the electrolytic deposition of a gold-copper-cadmium alloy, comprising a complex gold cyanide, a complex copper cyanide, cadmium ions, free potassium cyanide, a wetting agent as a brightener, and a complexing agent of the general formula

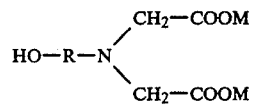

wherein R signifies an alkylene group having 1 to 4 carbon atoms, and M signifies sodium, potassium, or ammonium ions.

2. The solution of claim 1, wherein said complexing agent is chosen from the group consisting of hydroxymethylimino diacetic acid, hydroxyethylimino diacetic acid, hydroxypropylimino diacetic acid, and hydroxybutylimino diacetic acid.

3. The solution of claim 1, wherein said wetting agent is an alkyl polyglycol ether phosphate.

4. The solution of claim 3, wherein said wetting agent is a monoester having a molecular weight between 600 and 800.

5. The solution of claim 3, wherein said alkyl is a straight or branched chain having between 8 and 15 carbon atoms.

6. The solution of claim 1, further comprising a brightener in the form of an organic product having a molecule composed of a soluble salt of a phosphoric ester or diester of a chain of ethylene oxides bonded to an alkyl group, of the general formulae:

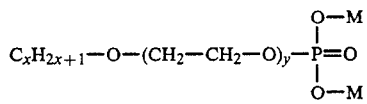

or

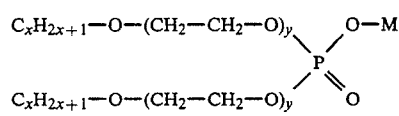

wherein x signifies a number between 8 and 18, y signifies a number between 6 and 15, and M signifies sodium, potassium, or ammonium ions.

7. The solution of claim 6, wherein said complexing agent is chosen from the group consisting of hydroxymethylimino diacetic acid, hydroxyethylimino diacetic acid, hydroxypropylimino diacetic acid, and hydroxybutylimino diacetic acid.

8. The solution of claim 1 wherein said wetting agent is a non-ionic one of the class of amidopropyldimethylaminoxides of fatty acids as a brightener.

9. The solution of claim 1, wherein said wetting agent has a molecular weight between 250 and 500.

10. The solution of claim 1, further comprising a surfactant in the form of one or a mixture of more than one amidopropyldimethylaminoxides of fatty acids of the general formula

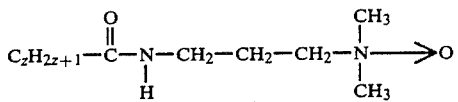

wherein z signifies a number between 11 and 17, as a brightener.

11. The solution of claim 10, wherein said complexing agent is chosen from the group consisting of hydroxymethylimino diacetic acid, hydroxyethylimino diacetic acid, hydroxypropylimino diacetic acid, and hydroxybutylimino diacetic acid.

12. The solution of claim 1, containing 1–20 g/liter of gold, 6–70 g/liter of copper, 0.3–5 g/liter of cadmium, 3–50 g/liter of free potassium cyanide, 0.1–50 g/liter of said wetting agent, and 5–100 g/liter of said complexing agent, and having a pH of between 9 and 11.

* * * * *